United States Patent [19]
Campana et al.

[11] Patent Number: 5,637,491
[45] Date of Patent: Jun. 10, 1997

[54] DEXTRANASE ENZYME, METHOD FOR ITS PRODUCTION AND DNA ENCODING THE ENZYME

[75] Inventors: Hernan R. Campana; Bianca M. Garcia Garcia; Julio M. Delgado Boada; Jose A. Cremata Alvarez; Maria E. Gonzalez Martinez; Emilio M. Clark; Dania M. Curbelo; Luis S. Herrera Martinez; Manuel R. Raices Perez-Castaneda; Efrain R. Jiminez; Rossana G. Fernandez; Vivian M. Cordova; Carlos F. Patron, all of Habana, Cuba

[73] Assignee: Centro de Ingenieria Genetica y Biotecnologia, Havana, Cuba

[21] Appl. No.: 354,618

[22] Filed: Dec. 13, 1994

[30] Foreign Application Priority Data

Dec. 14, 1993 [CU] Cuba ............................ 115/93

[51] Int. Cl.[6] .................................................. C12N 9/44
[52] U.S. Cl. .................. 435/211; 435/172.3; 435/320.1; 510/392; 510/530; 536/23.2
[58] Field of Search ................. 252/174.12; 435/211, 435/172.3, 320.1; 510/392, 530; 536/23.2

[56] References Cited

FOREIGN PATENT DOCUMENTS

0663443  7/1995  European Pat. Off. .

*Primary Examiner*—Paul Lieberman
*Assistant Examiner*—Kery A. Fries
*Attorney, Agent, or Firm*—Hoffmann & Baron

[57] ABSTRACT

A method for the isolation and expression of a gene coding for dextranase of the fungus *Penicillium minioluteum*. This enzyme of fungal origin is produced by expression at high levels in yeast. For this purpose, a cDNA copy of the mRNA coding for dextranase enzyme of the *Penicillium minioluteum* fungus was isolated and sequenced. This cDNA was transfered into *Pichia pastoris* cells. Recombinant yeasts capable of secreting dextranase to the culture medium were obtained thereby. The dextranase enzyme obtained can be used, e.g. in the sugar industry to hydrolyze the dextran in cane juices to increase the sugar production.

22 Claims, 4 Drawing Sheets

DEXTRANASE ENZYME, METHOD FOR ITS PRODUCTION AND DNA ENCODING THE ENZYME

FIELD OF THE INVENTION

This invention is in the field of genetic engineering and biotechnology and relates in particular to a method for the isolation and the expression in yeast of a gene coding for a dextranase.

BACKGROUND OF THE INVENTION

Dextranase (1,6-α-D-glucan 6-glucanohydrolase; EC 3.2.1.11) is an enzyme which hydrolyzes dextran. Dextran is a polymer of α-D glucopyranoses predominantly linked by 1,6 glycosidic bonds.

The initial interest in dextranase was its application in the commercial production of clinical dextran, used as blood substitute or extender (Tam, S. et al., 1976, Proc. Natl. Acad. Sci. USA. 73: 2128). Because of its ability to hydrolyze dextran, dextranase has also been found highly useful for hydrolyzing the dextran produced by the action of microorganisms causing dental caries or tooth decay. Thus, the incorporation of this enzyme into toothpaste or other oral detergent is considered in the art to provide a preventive or curative for tooth decay. See for example, the U.S. Pat. Nos. 3,991,177; 4,115,546; 4,140,758; 4,335,101; 4,438,093; 4,466,954; 4,469,673; 5,000,939; and 5,145,665.

In addition, dextranase is used in the sugar industry. Dextran is not a natural constituent of sugar juice, but it is formed by bacteria of the Leuconostoc species, which grow in damaged cane, and in juices that are delayed before processing through the evaporators. Dextran is a polymer which exhibits a high viscosity in solution. This increased viscosity becomes troublesome to both clarification and evaporation of juices and to the concentration of molasses when the level of dextran approaches 1000 parts per million of solid juices. Industrial dextranases are used to degrade the polymer to smaller molecules that do not create excessive viscosity. At a cane sugar refinery, dextran containing juice shows not only low filtration rate and poor crystallization of sucrose but also is the cause of serious quality problems of the final product.

Dextran is also formed occasionally in the processing of sugar beets, particularly when they have been exposed to freezing and thawing cycles during harvest and storage. The dextranase as described for cane sugar can be applied when this occurs.

The use of dextranase to hydrolyze dextran found in cane juices allows to increase the yield in sugar production (Imrie, F. K. E. et al., 1972, Sugar Technol. Rev. 1: 291–361; Fulcher, R. P. and Inkerman, P. A., 1976, Proc. Queensl. Soc. Sugar Cane Technol. 43: 295–305; Inkerman, P. A. and James, G., 1976, Proc. Queensl. Soc. Sugar Cane Technol. 43: 307–320; Inkerman, P. A. and Riddell, L., 1977, Proc. Queensl. Soc. Sugar Cane Technol. 44: 215–223; Inkerman, P. A., 1980, Proc. Int. Soc. Sugar Cane Technol. 17: 2411–2427; Barfoed, S. and Mollgaard, A., 1987, Zuckerindustrie (Berlin) 112(5): 391–395; Brown, C. F. and Inkerman, P. A., 1992, J. Agric. Food Chem. 40(2): 227–233).

Several microorganisms are capable of producing dextranase, among them fungi of the Penicillium, the Aspergillus, the Fusarium and the Chaetomium genera; Lactobacillus, Streptococcus and Flavobacterium bacteria, and yeasts such as the *Lipomyces starkeyi*, see for example, U.S. Pat. Nos. 2,742,399; 3,663,371; 3,875,009; 3,912,594; 4,732,854 and 4,820,640.

Commercial production of dextranase is by fermentation with either Penicillium sp. (Novo, 1977, Dextranase Novo 25L. A dextran decomposing enzyme for the sugar industry. Product data information 112-GB, Novo Enzyme Division, Hagsvaerd, Denmark) or Chaetomium sp. (Miles, 1986, Dextranex. Fungal dextranase for the sugar cane industry. Technical information L-1475, Miles Laboratories, Inc. Elkhart, Ind., USA). However, none of these fungi constitute an enzymatic source accepted by the U.S. Food and Drug Administration (FDA) (Koenig, D. W. and Day, D. F., 1989, Applied and Environmental Microbiology 55(8): 2079–2081).

Yeast, meanwhile, is a microorganism widely used in the food industry and most recently, in the production of pharmaceutical products. Yeast can also grow to a high cellular density in less time than fungi and it is therefore an appropriate host for industrial production of secreted proteins.

Only three groups have reported the cloning of genes coding for dextranases from different bacteria (Barrett, J. F. et al., 1987, Infection and Immunity 55(3): 792–802; Lawman, P. et al., 1991, Journal of Bacteriology 173(23): 7423–7428 and Okushima, M. et al., 1991, Jpn. J. Genet. 66: 173–187) and of these, only one nucleotide sequence has been published (Okushima, M. et al., 1991, Jpn. J. Genet. 66: 173–187). Neither reports about molecular cloning or sequencing of any fungal gene coding for dextranase nor works about the heterologous expression of dextranase in yeast have been published.

SUMMARY OF THE INVENTION

The novelty of this invention is the identification of the nucleotide sequence which codes for a dextranase of the fungus *Penicillium minioluteum* and its expression in the yeast *Pichia pastoris* to obtain high levels of this enzyme in secreted form. The enzyme produced in *Pichia pastoris* cells is characterized in that it has a higher thermal stability than the natural fungal enzyme from *Penicillium minioluteum*. The new recombinant strain can be used in the industrial production of dextranase. In view of sequencing data (Seq. Id. No. 1), this new nucleotide sequence coding for a fungal dextranase is not homologous to the nucleotide sequence which codes for bacterial dextranase reported by Okushima et al., 1991, Jpn. J. Genet. 66: 173–187.

The technical solution of this invention is related to the establishment of the nucleotide sequence of a cDNA copy of mRNA coding for a dextranase enzyme isolated from the *Penicillium minioluteum* fungus (Seq. Id. No. 1 and Seq. Id. No. 2). The dextranase cDNA was transferred to a *Pichia pastoris* expression vector and this recombinant plasmid was used to obtain yeast transformants capable of secreting high dextranase levels.

DETAILED DISCLOSURE OF THE INVENTION

In a first aspect, the present invention provides an isolated and purified DNA having a nucleotide sequence which essentially corresponds to or hybridizes with a nucleotide sequence comprised in the dextranase gene, shown in Seq. Id. No. 1, of the fungus *Penicillium minioluteum*.

The words "a nucleotide sequence comprised in the dextranase gene" are intended to include several possibilities. One option is a DNA which covers the complete dextranase gene, i.e. the gene inclusive of regulatory and coding sequences. Another option is a DNA essentially consisting of the coding sequence, or a part of the coding sequence, and lacking the dextranase promoter region. One such possibility is a dextranase cDNA obtained by reverse transcription from dextranase mRNA. The invention also covers a DNA essentially consisting of the dextranase promoter and lacking the dextranase coding region. Furthermore, the invention relates to oligonucleotides of sufficient length to be specific for dextranase DNA or RNA. Such oligonucleotides may be useful as dextranase-specific probes or primers and will usually have a length of from about 7 or 8, preferably from about 9 or 10 nucleotides up to about 40 or 50 nucleotides, preferably to about 25 or 30 nucleotides, or above 50 nucleotides up to the complete length of the gene.

The words "a nucleotide sequence which essentially corresponds to or hybridizes with" are intended to include single stranded and double stranded DNA. In the case of single stranded DNA, both the corresponding and the complementary sequence are intended to be included by this wording.

The correspondence need not be 100%, i.e. DNA having a certain homology to the sequence shown in Seq. Id. No. 1 is intended to be included. DNA which has a homology of at least 60%, preferably a homology of at least 70% to said sequence is intended to be covered. It is especially intended to cover DNA having the same function and/or effect, even though the sequence differs from the one shown in Seq. Id. No. 1. Therefore, changes in the dextranase promoter region which do not affect the promoter function of said sequence are intended to be covered by this invention. Similarly, the invention is intended to include any changes in the dextranase coding region which either lead to the same amino acid sequence or to an amino acid sequence which, notwithstanding one or more deviations from the original amino acid sequence, maintains dextranase activity.

For example, the invention intends to cover not only the genomic DNA and cDNA which codes for the dextranase enzyme of the fungus *Penicillium minioluteum* but also DNA encoding related dextranase enzymes, such as DNA coding for the dextranase enzyme of related fungi, such as *Penicillium funiculosum*, *Penicillium aculeatum* and *Penicillium pinophilum*. Dextranase enzymes are considered to be related when they have a similar dextranase activity, and/or are recognized by the same anti-dextranase antibody, and/or are encoded by DNA having a homology of at least 60 or 70%.

According to a preferred embodiment of the invention, the DNA comprises a nucleotide sequence coding for an enzyme having dextranase activity. Preferably, said nucleotide sequence codes for the dextranase enzyme of the fungus *Penicillium minioluteum*. Said nucleotide sequence essentially codes for the amino acid sequence shown in Seq. Id. No. 2. More specifically, said nucleotide sequence essentially consists of the nucleotides #1226 to #2947 of Seq. Id. No. 1.

According to another preferred embodiment of the invention, said DNA comprises a nucleotide sequence from the promoter region of the dextranase gene of the fungus *Penicillium minioluteum*. More preferably, said nucleotide sequence essentially consists of nucleotides within the region of the nucleotides #1 to #1079 of Seq. Id. No.1.

A further aspect of the present invention provides a recombinant polynucleotide comprising a DNA as defined above (a dextranase-specific DNA) and a nucleotide sequence of a cloning or expression vector, wherein said polynucleotide is able to direct the expression of a protein in a suitable host. Preferably, said recombinant polynucleotide is able to direct expression of a protein with dextranase activity in a suitable host, said host preferably being a yeast, especially the yeast *Pichia pastoris*. A particularly preferred example of a recombinant polynucleotide able to direct expression of a dextranase enzyme in yeast such as *Pichia pastoris* is the plasmid pPDEX1.

A further aspect of this invention is a host cell transformed with a recombinant polynucleotide as defined above. Preferably, said host cell is a yeast, especially the yeast *Pichia pastoris*. A particularly preferred example of such a host cell is *Pichia pastoris* strain MPDEX1.

An important further aspect of this invention is a proteinaceous substance having dextranase activity, said substance comprising a polypeptide having essentially an amino acid sequence as shown in Seq. Id. No. 2, or a fragment of the same. By the use herein of the term "essentially" it is intended to cover all proteinaceous substances having a homology of at least 60%, and preferably at least 70%, to said Seq. Id. No. 2. In a particularly preferred embodiment of the present invention, the proteinaceous substance with dextranase activity has an optimum temperature for the enzymatic activity in a range between 55° and 60° C. as well as an N-glycosylation percentage between 13 and 15% and a half-life time of about 7.6 hours at 50° C.

The invention covers the enzyme irrespective of how it has been produced, for example by recombinant DNA/ genetic engineering technology, chemical synthesis, enzymatic degradation, or a combination thereof. Further, the invention not only covers the enzyme as such, but also in the form of fusion proteins having dextranase activity.

Another aspect of this invention is a method for producing a proteinaceous substance having dextranase activity, comprising expression in yeast of a DNA as defined herein which codes for a dextranase enzyme. Preferably, said expression is in the yeast *Pichia pastoris*. This invention includes a method as defined herein, wherein the dextranase enzyme produced is isolated from the growth medium.

The invention also provides a method for hydrolyzing dextran comprising contacting dextran under suitable dextran depolymerization conditions with a dextranase enzyme or with cells producing a dextranase enzyme and optionally recovering the dextran depolymerization products produced, wherein said dextranase enzyme is a proteinaceous substance as defined herein or a proteinaceous substance obtained by a method as defined herein.

Strain Deposits

The plasmid pPS7 was deposited on 22 August 1994 under the provisions of the Budapest Treaty with the Belgian Coordinated Collections of Microorganisms (BCCM-LMBP-Collection) and received accession number LMBP3116.

The strains *Penicillium minioluteum* Dierckx (HI-4) and *Pichia pastoris* MP36 were deposited on 22 August 1994 under the provisions of the Budapest Treaty with the Mycothèque de l'Université Catholique de Louvain (MUCL), Belgium, and received accession numbers MUCL 38929 and MUCL 38930, respectively.

EXAMPLES

These examples intend to illustrate the invention, but not to limit the scope of this invention.

Example 1: Dextranase Induction Kinetics; in Vitro Translation of the mRNA and Immunoprecipitation of the Translation Products The dextranase induction kinetics of a *Penicillium minioluteum* fungus were performed in a 5 l fermenter B. E. Marubishi (Tokyo, Japan) with 3.5 l effective capacity containing medium composed of 0.7% $NaNO_3$; 0.07% $MgSO_4 \cdot 7H_2O$; 0.35% $KH_2PO_4$; 0.002% yeast extract and 2% native dextran obtained from a *Leuconostoc mesenteroides* culture (Raíces, M. et al., 1991, Biotecnologia Aplicada 8(2): 248–255).

Dextranase induction studies for other microorganisms have shown the absence of enzymatic activity in cultures containing glucose as carbon source (Fukumoto, J. et al., 1971, J. Biochem. 69: 1113–1121; Simonson, L. G. et al., 1975, Mycology 67: 845–851; Madhu, M. et al., Enzyme Microb. Technol. 6: 217–220). To analyze the effect of glucose on the enzyme induction in this fungus, a culture was prepared, adding 2% glucose instead of dextran.

The fermenters were inoculated with mycelium washed with 0.9% NaCl and the fermentation was carried out for 100 hours while maintaining the temperature at 28° C., the pH at 5.5, the stirring speed at 300 rpm and the aeration rate at 1 vvm (volumes per min.). The dextranase activity was determined according to Kosaric et al. (1973, Biotech. Bioeng. XV: 729–741). One unit (1 U) of dextranase is defined as the amount of enzyme that liberates 1 μmole of glucose equivalents in one minute from T-2000 dextran (Pharmacia) at pH 5° and 40° C. The reducing sugars were determined colorimetrically with dinitrosalicylic acid reagent (DNSA method), (Miller, G. L., 1959, Anal. Chem. 31: 426–428).

The dextranase enzymatic activity in the dextran-culture was detected after 40 hours of fermentation, following an increase in this activity until a value of 380 U/ml of culture. Meanwhile the culture grown in glucose did not show dextranase activity. The presence of the enzyme was also observed through electrophoresis in 12.5% polyacrylamide gel (PAGE) with 1% blue-dextran (Pharmacia) and by Western blotting (Towbin, H. et al., 1979, Proc. Natl. Acad. Sci. U.S.A. 76: 4350–4354; Maniatis, T. et al., 1989, Molecular Cloning, CSH, N.Y., USA) using a polyclonal antibody prepared in a rabbit immunized against purified dextranase from the fungus *Penicillium minioluteum* (Raíces, M. et al., 1991, Biotecnología Aplicada 8(2): 248–255). Both methods corroborated the presence of the enzyme only in the dextran induced culture after 40 hours of the fermentation.

The fungus mycelium grown in dextran or glucose mediums as carbon sources was collected through centrifugation at different fermentation times (48, 56 and 72 hours) and the total cellular RNA was isolated using the guanidinium thiocyanate extraction method described by Chirgwin et al. (1979, Biochem. 18: 5294–5299). The Poly $(A)^+$ fraction was purified by chromatography through an oligo (dT) cellulose column (Sigma Chemical Company, USA) according to the method of Avid and Leder (1972, Proc. Natl. Acad. Sci. USA 69: 1408–1412) and the different fractions were translated in vitro in rabbit reticulocyte lysates (Rabbit reticulocyte lysate, nuclease treated, Promega) using $^{35}S$-methionine (Ahersham). The translation products were immunoprecipitated as described by Dobberstein et al. (1979, Cell 17: 759–769) with antidextranase immunoserum and the immunoprecipitates were analyzed by SDS-polyacrylamide gel electrophoresis.

The in vitro translation of the Poly $(A)^+$ RNAs isolated from the culture grown in dextran showed two polypeptides of similar molecular weight that were immunoprecipitated by the anti-dextranase polyclonal antibody. These polypeptides are abundant in the mRNA population isolated at 56 hours and their molecular weight is slightly lower than that of the natural purified dextranase from *Penicillium minioluteum* (67 kDa). The mRNA isolated from the culture grown in glucose did not lead to the synthesis of polypeptides that were immunoprecipitated by the antidextranase antibody.

Example 2: Isolation of cDNA Coding for *Penicillium minioluteum* Dextranase

Based on the in vitro translation and immunoprecipitation results, 5 μg of Poly $(A)^+$ RNA of the 56 hour culture growth were used to synthesize cDNA using the Stratagene cDNA synthesis kit (Huse, W. D. et al., 1988, Strategies 1: 1–3). This cDNA was then ligated to the EcoRI-XhoI digested pBluescript II SK (Short, J. M. et al., 1988, Nucleic Acids Research 16: 7583) and the ligation product was transformed into *E. coli* strain MC1061 (Meissner, P. S. et al., 1987, Proc. Natl. Acad. Sci. U.S.A. 84: 4171), thus constructing a cDNA library from the dextran-induced culture.

The cDNA clones corresponding to genes differentially regulated in the induced culture (grown in dextran) in relation to the non-induced culture (grown in glucose) were isolated by differential screening (plus-minus) as described by Maniatis et al. (1989, Molecular Cloning, CSH, N.Y., U.S.A.). Two cDNA probes labeled with $^{32}P$ were synthesized from 1 μg of the Poly $(A)^+$ RNAs at 56 hours of the induced and non-induced cultures using $[\alpha\text{-}^{32}P]$ dATP (Amersham). The radiolabeled probes were hybridized separately to duplicate copies of the same cDNA library. Those clones were selected that hybridize to only the cDNA probe from the induced culture. Crossed hybridization among the clones enabled identification of four different nonhomologous groups which are represented in the library at 2.1%, 1.3%, 0.4% and 0.25%. The Northern blotting analysis (Maniatis, T. et al., 1989, Molecular Cloning, CSH, N.Y., U.S.A.) of the induced and non-induced Poly $(A)^+$ RNAs using as a probe one cDNA fragment from each group of clones confirmed that these cDNA fragments correspond to genes that are expressed differentially in these cell cultures (induced and non-induced), since each probe hybridized only to the Poly $(A)^+$ RNA from dextran-induced culture.

In order to identify the dextranase cDNA clone, the T7 RNA polymerase-promoter expression system developed by Studier and Moffat (1986, J. Mol. Biol. 189: 113) was used. For this purpose a cDNA fragment selected for each of the four groups of clones was subcloned into pET-3a, pET-3b and pET-3c vectors, resp. (Studier, F. W. et al., 1990, Methods Enzymology 185; Maniatis, T. et al., 1989, Molecular Cloning, CSH, N.Y., U.S.A.). These vectors were previously cleaved with BamHI and the ends were filled in with the Klenow fragment and treated with alkaline phosphatase (Boehringer Mannheim).

The pET-3a, pET-3b, and pET-3c vectors ligated to cDNA inserts were transformed into $E.\ coli$ strain BL21(DE3) pLysS by selection for resistance to ampicillin and chloramphenicol. BL21(DE3) pLysS is a lysogen bearing the bacteriophage T7 polymerase gene under the control of the lacUV5 promoter and also carries the pLysS plasmid which confers resistance to chloramphenicol and produces T7 lysozyme, increasing the host tolerance for toxic target plasmids (Moffat, B. A. et al., 1987, Cell 49: 221–227; Inouye et al., 1973, J. Biol. Chem. 248: 7247; Studier, F. W. et al., 1990, Methods Enzymology 185).

The cDNA fragments joined to the beginning of the gene10 of T7 bacteriophage were expressed in BL21(DE3) pLysS as fusion proteins after inducing the system with IPTG (isopropylthio-β-D galactoside) at a 1 mM final concentration. The Western blotting analysis evidenced a protein that was recognized by the anti-dextranase polyclonal antibody, being this protein produced by a transformant containing the pETDEX plasmid that was constructed by subcloning the HincII cDNA fragment from pBCDEX plasmid into pET-3a vector. This result shows that the pBCDEX plasmid contains a cDNA which codes for the $Penicillium$ $minioluteum$ dextranase and this cDNA corresponds to the group of clones most represented in the library (2.1%).

The dextranase cDNA nucleotide sequence contains four ATG's located in the 5' region of this sequence (see Seq. Id. No. 1) representing possible translation start sites, since the reading frame they originate coincides with the one determined by the pETDEX plasmid sequence (Sanger, F. et al., 1977, Proc. Natl. Acad. Sci. U.S.A. 74: 5463–5467) with which the dextranase protein expression was obtained in $E.$ $coli$.

The N-terminal region of dextranase secreted to the medium by $Penicillium\ minioluteum$ was subjected to the Edman degradation method (Edman, P., 1950, Acta Chem. Scand. 4: 283–293). A fraction of this purified protein (Raices, M. et al., 1991, Biotecnologia Aplicada 8(2): 248–255) was applied to a PVDF (polyvinylidene difluoride, Millipore) filter previously activated with methanol. The Edman degradation was carried out according Silva et al. (European Patent Application 0 474 313 A2) using the Knauer's Automatic Sequencer, model 810, connected to an HPLC (High Performance Liquid Chromatography) system, so as to detect the phenylthiohydantoin derivatives of the amino acids (PTH-amino acids). This technique elucidated the N-terminal sequence of the molecule to be: Met Gly Thr Thr Asn Asn Thr His Cys Gly Ala Asp Phe Cys Thr Trp (Seq. Id. No. 3).

This sequence matches with the sequence of the first 16 amino acids translated from the fourth ATG identified in the dextranase cDNA nucleotide sequence (Seq. Id. No. 1 and Seq. Id. No.2). When the amino acid sequence translated from the cDNA sequence between the first or second ATG to the fourth ATG (Seq. Id. No. 1) was analyzed, the following common characteristics for signal peptides can be noted: the amino-terminal region is followed by a larger highly hydrophobic region which could have an α-helix conformation, it being flanked at its carboxyl terminus by a slightly hydrophilic region.

Example 3: Molecular Cloning of Dextranase Genomic DNA

Chromosomal DNA from $Penicillium\ minioluteum$ was isolated using the method described by Raeder and Broda (1985, Lett. Appl. Microb. 1: 17–20) and analyzed by Southern blotting. The genomic DNA was digested with BamHI and hybridized to a probe containing a dextranase cDNA sequence. The analysis showed only one band of about 9 kb and this result was used as a basis for constructing a genomic library in $E.\ coli$.

The chromosomal DNA digested with BamHI was fractionated by sedimentation through a 10–40% sucrose gradient according to Maniatis et al. (1989, Molecular Cloning, CSH, N.Y., U.S.A.). DNA fragments of an appropriate size (over 6 kb) were ligated to pUC19 (Yanisch-Perron, C. et al., 1985, Gene 33: 103–119) vector (previously cleaved with BamHI and treated with phosphatase) and transformed into $E.\ coli$ strain MC1061 (Meissner, P. S. et al., 1987, Proc. Natl. Acad. Sci. U.S.A. 84: 4171).

The genomic clone was identified in this library by hybridization with the dextranase cDNA probe. The isolated recombinant plasmid was digested with BamHI, showing that the size of the genomic insert (9 kb) corresponds to the size obtained previously by Southern blotting analysis of chromosomal DNA.

A fragment of 3629 bp contained in the genomic BamHI insert which includes the dextranase gene was sequenced (Seq. Id. No. 1) using the method described by Sanger et al. (1977, Proc. Natl. Acad. Sci. U.S.A. 74: 5463–5467). From the comparison of the cDNA and genomic sequences we arrived to the conclusion that the $Penicillium\ minioluteum$ dextranase gene does not include introns in its nucleotide sequence.

Example 4: Homology among Dextranase Genes of different Fungi which produce this Enzyme To examine the existing homology between the dextranase gene of $Penicillium\ minioluteum$ and analogous genes of other dextranase producing fungi, the following fungi strains from the IMI (International Mycological Institute) collection were used:

1. $Paecilomyces\ lilacinus$ (IMI 027 830);
2. $Penicillium\ funiculosum$ (IMI 040 235);
3. $Penicillium\ aculeatum$ (IMI 040 588);
4. $Penicillium\ pinophilum$ (IMI 087 160);
5. $Penicillium\ verruculosum$ (IMI 079 196).

These strains were grown in a rice medium (rice grains washed and sterilized for 15 min. at 121° C.) to induce sporulation and the spores were used as inoculum to develop biomass in liquid YPD (1% yeast extract, 2% peptone and 2% glucose) medium, pH 5 at 23° C. for 48 hours. The biomass collected was used to isolate chromosomal DNA as described by Raeder and Broda (1985, Lett. Appl. Microb. 1: 17–20). The chromosomal DNA isolated from each strain was analyzed by Southern blotting according to Maniatis et al. (1989, Molecular Cloning, CSH, N.Y., U.S.A.). Genomic DNAs were digested with BamHI and hybridized to a probe containing the dextranase cDNA sequence from the $Penicillium\ minioluteum$ fungus. The hybridization bands observed as a result of Southern blotting demonstrate that there is a high homology between the dextranase genes of the *Penicillium funiculosum* (IMI 040 235), the *Penicillium aculeatum* (IMI 040 588), the *Penicillium pinophilum* (IMI 087 160) and the isolated *Penicillium minioluteum* dextranase gene. However no hybridization signals were observed for chromosomal DNAs corresponding to *Paecilomyces lilacinus* (IMI 027 830) and *Penicillium verruculosum* (IMI 079 196) fungi.

In order to assess whether the dextranases produced by these fungi are recognized by the polyclonal antibody obtained against dextranase protein purified from *Penicillium minioluteum* (Example 1), a total of $10^6$ spores were used as inoculum for 200 ml of a liquid medium solution composed of 0.7% $NaNO_3$; 0.07% $MgSO_4 \cdot 7H_2O$; 0.35% $KH_2PO_4$; 0.002% yeast extract and 2% native dextran obtained from a *Leuconostoc mesenteroides* culture (Raíces, M. et al., 1991, Biotecnologia Aplicada 8(2): 248–255). Cultures were incubated for 100 hours at 26° C. and the dextranase activity was detected in the culture supernatant fluids.

To recover the dextranase enzyme, the supernatants were concentrated and salted out. For this purpose the supernatants were freeze-dried and resuspended in 10 ml of distilled water to carry out a dialysis in distilled water. Subsequently the samples were freeze-dried, resuspended in 1 ml of distilled water and salted out on a P2 column (Biorad, U.S.A.).

The Western blotting analysis of the samples corresponding to *Penicillium funiculosum* (IMI 040 235), *Penicillium aculeatum* (IMI 040 588) and *Penicillium pinophilum* (IMI 087 160) evidenced protein bands of similar molecular weight (67 kDa) recognized by the antidextranase polyclonal antibody obtained against the *Penicillium minioluteum* dextranase protein. Consequently the dextranase enzymes that were recognized by the antidextranase antibody are produced by the same fungi that evidenced DNA homology with the *Penicillium minioluteum* dextranase gene.

Example 5: Expression of cDNA coding for *Penicillium minioluteum* Dextranase in *Pichia pastoris*

The cDNA coding for dextranase was amplified from the pBCDEX plasmid by PCR (Polymerase Chain Reaction). The amplified fragment starting from the fourth ATG (corresponding to the N-terminus of the dextranase secreted by *Penicillium minioluteum* fungus; see example 2) was inserted into pPS7 vector being fused to the SUC2 gene signal sequence from *Saccharomyces cerevisiae* to be expressed in the methylotrophic yeast *Pichia pastoris* under the control of the methanol-controlled alcohol oxidase (AOX1) promoter used for the expression of foreign proteins in this host (European Patent Application 438 200 A1).

The pPS7 plasmid (FIG. 1) is a *Pichia pastoris* integrating vector designed for the heterologous gene expression in this host. This plasmid is a derivative from pUC18 (Yanisch-Perron, C. et al., 1985, Gene 33: 103–119) that can replicate in *E. coli* and carries the ampicillin resistance gene. In addition, this vector also contains a 1.15 kb fragment (PAOX1) of the methanol-controlled alcohol oxidase promoter followed by the SUC2 gene signal sequence (sp SUC2) from *Saccharomyces cerevisiae*, the transcription terminator sequence (GAPt) of the glyceraldehyde-3-phosphate dehydrogenase gene from *Saccharomyces cerevisiae*, the *Saccharomyces cerevisiae* HIS3 gene, and the 3' region (2.1 kb) of the AOX1 gene (3'AOX1). This vector was cleaved with NcoI, made blunt ended with Mung Bean nuclease and treated with alkaline phosphatase (Boehringer Mannheim) according to Maniatis et al. (1989, Molecular Cloning, CSH, N.Y., U.S.A.).

Figure 1:
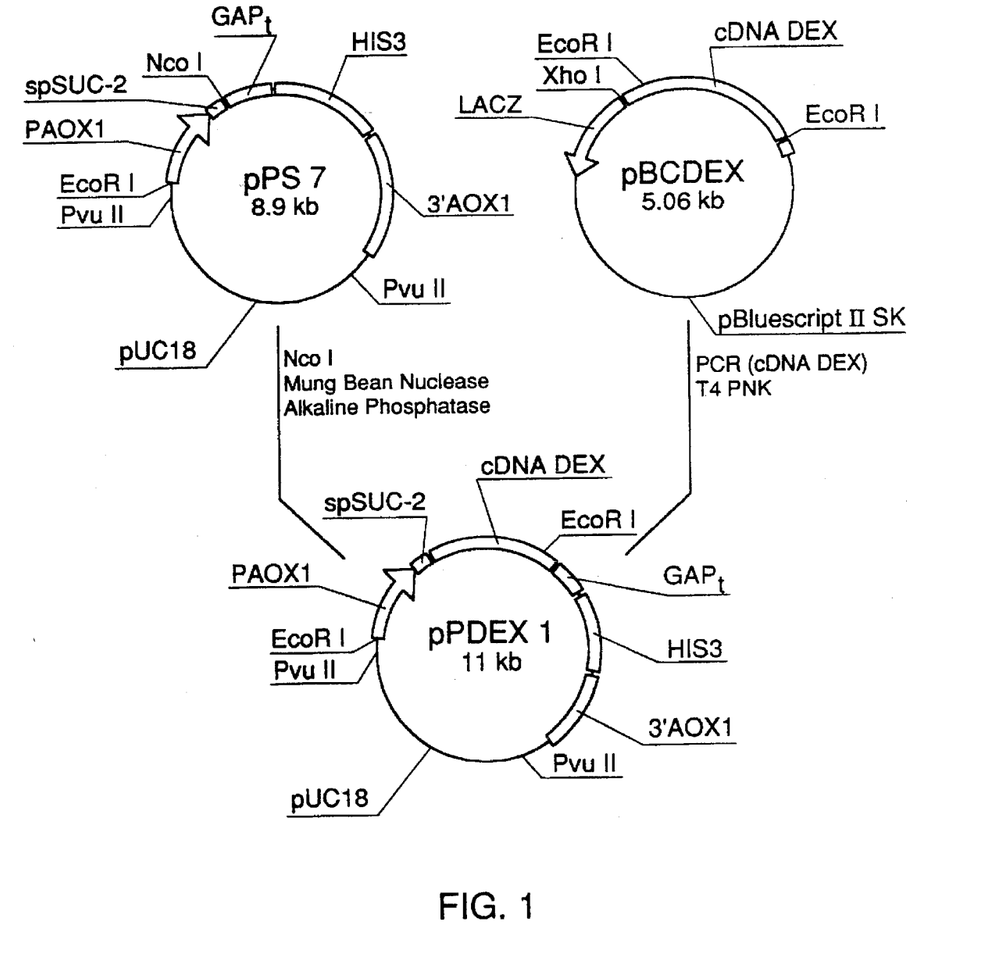
FIG. 1 Construction of plasmid pPDEX1 for expression of dextranase cDNA from *Penicillium minioluteum* in *Pichia pastoris*.

Two oligonucleotides primers: DX1: 5'-ATGGGCACTACGAATAATACCCAT (Seq. Id. No. 4) and DX5: 5'-GGAAACCTGGAAATGTCCTTAT (Seq. Id. No. 5) were used to isolate the dextranase cDNA by PCR from pBCDEX plasmid according to Saiki et al. (1988, Science 239: 487–491). The isolated fragment was phosphorylated using T4-polynucleotide kinase and subcloned into the pPS7 vector (FIG. 1).

The plasmid pPDEX1 (FIG. 1) constructed by subcloning the dextranase cDNA into the pPS7 vector was digested with PvuII and transformed into the *Pichia pastoris* mutant strain MP36 (his3⁻) using the electroporation method described by Meilhoc et al. (1990, Bio/Technology 8: 223–227). Transformants were selected for their ability to grow on G medium (Galzy, P. and Slonimski, P. P., 1975, C. R. Acad. Sci. Paris 245: 2423–2427) containing 2% glucose (histidine-deficient medium) by complementation of the mutation his3⁻ $^{in}$ *Pichia pastoris* with the HIS3 gene from *Saccharomyces cerevisiae* (Yong, V. et al., 1992, Biotecnologia Aplicada 9: 55–61). The grown colonies were transferred to a plate containing G medium and 0.4% blue-dextran (Pharmacia) and the dextranase expression was induced with methanol vapor. Few hours after induction, the transformants formed halos of dextran hydrolysis.

The dextranase expression was studied in shake flasks with 15 transformants which evidenced activity in blue-dextran plates. Cells grown for 22 hours at 30° C. in 50 ml of G medium containing 2% (v/v) glycerol were centrifuged, washed and resuspended in the same medium containing 1% (v/v) methanol instead of glycerol for further incubation. During growth, 0.5% (v/v) methanol was added every 12 hours for a total of 100 hours.

The dextranase activity in the culture supernatant samples was determined as described previously in the example 1. All the transformants showed a progressive increase in the activity of the culture supernatant after methanol induction. The MPDEX1 transformant yielded 100 U/ml of dextranase activity in the culture supernatant and was selected for further dextranase expression studies. The chromosomal DNA isolated from the MPDEX1 strain and digested with EcoRI was analyzed by Southern blotting. The analysis clearly shows that the transforming DNA disrupted the AOX1 locus by double crossover recombination.

The dextranase expression in the MPDEX1 strain was studied also in a 5 l laboratory-scale fermenter (3.5 l working volume) B. E. Marubishi (Tokyo, Japan) containing industrial medium (0.13% $(NH_4)_2HPO_4$, 0.09% $(NH_4)_2SO_4$, 0.05% urea and molasses which yield 4% total reducing sugars). The fermenter was inoculated to $OD_{530}$=C.2 and when the $OD_{530}$ reached a value of 60, the culture was induced with methanol. The methanol feed rate was gradually increased to 3.5 g/h per liter of culture during 120 hours of growth. During the fermentation process the stirring speed was increased from 350 rpm to 750 rpm, maintaining the temperature at 30° C., the pH at 5.2 and the aeration rate at 1 vvm (volumes per min.).

The dextranase activity in the culture supernatant increased progressively after methanol induction, reaching 2500 U/ml (2.6 grams of dextranase secreted to the growth medium per liter of culture). After subjecting the cells to mechanical lysis with glass beads according to Maniatis et al. (1989, Molecular Cloning, CSH, N.Y., U.S.A.), it was noted that the amount of dextranase secreted to the growth medium was 85% of the total amount produced by the cells. Consequently the secretion of dextranase to the growth medium is efficient in this host. These results show that the level of dextranase secreted to the growth medium by this recombinant yeast (2500 U/ml; 2.6 g/l) is significantly greater than the level secreted by the *Penicillium minioluteum* fungus (380 U/ml; 0.4 g/l) in approximately the same time of fermentation at a 3.5 l scale.

The upscaling process was performed in a 300 l fermenter (200 l working volume) B. E. Marubishi (Tokyo, Japan) containing industrial medium. The fermenter was inoculated to $OD_{530}$=0.2 and when the $OD_{530}$ reached a value of 70, the culture was induced with methanol. The methanol feed rate was gradually increased to 3.5 g/h per liter of culture during 80 hours of growth. During the fermentation process the stirring speed was increased from 350 rpm to 750 rpm, maintaining the temperature at 30° C., the pH at 5.2, the dissolved $O_2$ at 20% and the aeration rate at 1 vvm. After induction with methanol, in this upscaling process the extracellular dextranase activity increased up to 2700 U/ml (2.8 g/l) in 100 hours of fermentation.

Example 6: Structural Characterization of Recombinant Dextranase expressed in *Pichia pastoris* and its comparison with Natural Dextranase from the *Penicillium minioluteum* Fungus The recombinant enzyme was purified from the fermentation culture supernatant (example 5) by consecutive centrifugations at 8000 rpm for 15 min. before and after heating for 1 hour at 50° C. The supernatant was dialyzed against 10 mM ammonium acetate (pH 5) buffer and applied to an FFQ (125×18 mm) anion exchange column (Pharmacia) equilibrated with the same buffer. The protein was eluted with a linear gradient of 10 to 750 mM ammonium acetate (pH 5) at 1 ml/min. flow rate. The obtained chromatogram showed a non retained fraction and a major peak which eluted at 50 min. retention time, after applying the gradient. The major peak was the only one which showed dextranase activity and a single band in SDS polyacrylamide gel electrophoresis (PAGE-SDS), and in Western blotting using rabbit antidextranase antibody (example 1) or recognition with a specific lectin for mannosylation, Concanavalin A: Horse radish peroxidase (Con A: HRP). Both electrophoresis and Western Blotting showed a double band for the natural product as was reported by Raices et al. (1991, Biotecnologia Aplicada 8(2): 248–255) while the recombinant product shows only a single band similar to the heavier one observed in natural dextranase. It was also determined that the recombinant enzyme maintains the same specific activity as the natural enzyme in the range of 950–1000 U/mg protein.

According to the determination of total carbohydrates by the phenol-sulphuric acid method (Dubois, M. et al., 1956, Anal. Chem. 28: 350), it was estimated that the glycosylation percentage of the natural enzyme was 4–5%, while 13–15% for the recombinant enzyme (approximately 3 times higher). The glycosylation detected was mainly N-linked with oligomannoside structures as showed the identification assays with Con A : HRP and also deglycosylation with PNGase F (Boehringer Mannheim). These assays also showed that there are only a few N-glycosylation sites because the difference in size was small between the native enzyme and the deglycosylated one when treated with Endo H and PNGase F, which coincides with the results inferred from the amino acid sequence of the protein (Seq. Id. No. 2) deduced from the nucleotide sequence, where only three N-glycosylation sites were located. Furthermore, by means of a DIG glycan differentiation kit (Boehringer Mannheim) it was demonstrated that there is not any O-glycosylation.

The N-terminal sequences of both natural and recombinant dextranase were identical according to Edman's automatic degradation (example 2). Comparison of peptide maps of both proteins digested with trypsine (Boehringer Mannheim) at an enzyme : substrate ratio of 1:100 (p/p) in 100 hum phosphate buffer (pH 8), at 37° C. for 4 hours and fractionated in a C4 reverse phase HPLC column (4.6×250 mm) with a linear gradient of 1 to 60% acetonitrile with 0.05% TFA for 120 min., showed that in both cases the principal fragments had the same retention time and a very similar general elution profile. Some fragments were selected from the recombinant enzyme chromatogram and sequenced by Mass Spectrometry using Xenon Fast Atom Bombardment as ionization source (FAB/MS). Some peptides were submitted to "linked scan" (simultaneous electric and magnetic field scanning) for sequencing according Gonzalez et al. (1992, Analytical Biochemistry 205: 151–158). Peptide sequences corresponded with fragments of the dextranase gene translated sequence (Sec. Id. No. 2).

Example 7: Biochemical Characterization of Recombinant Dextranase and its comparison with the Natural Enzyme of *Penicillium minioluteum* Fungus a) Km and Vmax Determinations Dextran T-2000 (Pharmacia) depolymerization kinetics were performed at 25° C. at a constant enzyme concentration of 0.1276 U per ml, with the substrate concentration varying from 0.8 to 3.5 mg/ml. The remaining dextran concentration was determined by the Nicholson-Horsley turbidity test (1959, J. Agr. Food Chem. 7: 640–643). The initial depolymerization rates (IDR, in mg dextran per ml per min.) were calculated by adjusting the reaction rate to a first order reaction for substrate concentrations from 0.8 to 2.6 mg/ml and to a zero order for substrate concentrations greater than 2.6 mg/ml.

Figure 2:
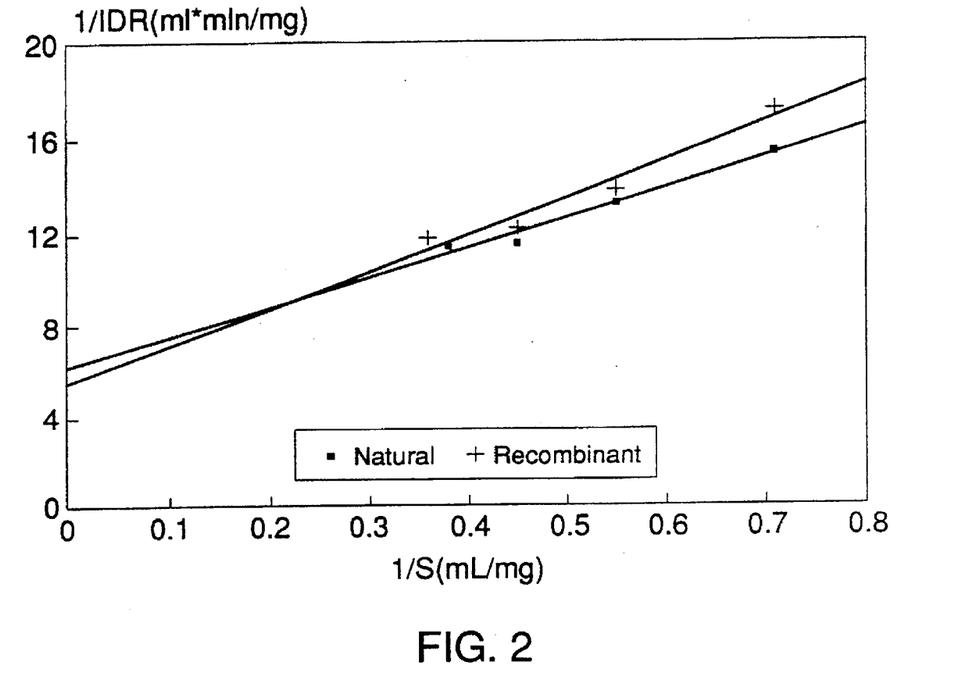
FIG. 2 Double reciprocal representation of the Michaelis-Menten equation (Lineweaver-Burk modification) applied to the initial dextran depolymerization rate (IDR) values using natural and recombinant dextranase.

The Lineweaver-Burk modification of Michaelis-Menten's equation was applied to the former data (FIG. 2) to estimate Km and Vmax values, both for natural and recombinant enzymes. It was evidenced that these kinetic parameters were the same for both enzymes as it is shown in Table 1.

TABLE 1

Comparison of kinetic parameters Km and Vmax for natural (*Penicillium minioluteum*) and recombinant dextranase (MPDEX1).

| Enzyme | Km (mg/ml) | Vmax (mg/ml.min.) |
|---|---|---|
| Natural | 2.05 | 0.161 |
| Recombinant | 2.12 | 0.153 | b) Influence of pH on Enzymatic Activity; Stability at Different pH

Figure 3:
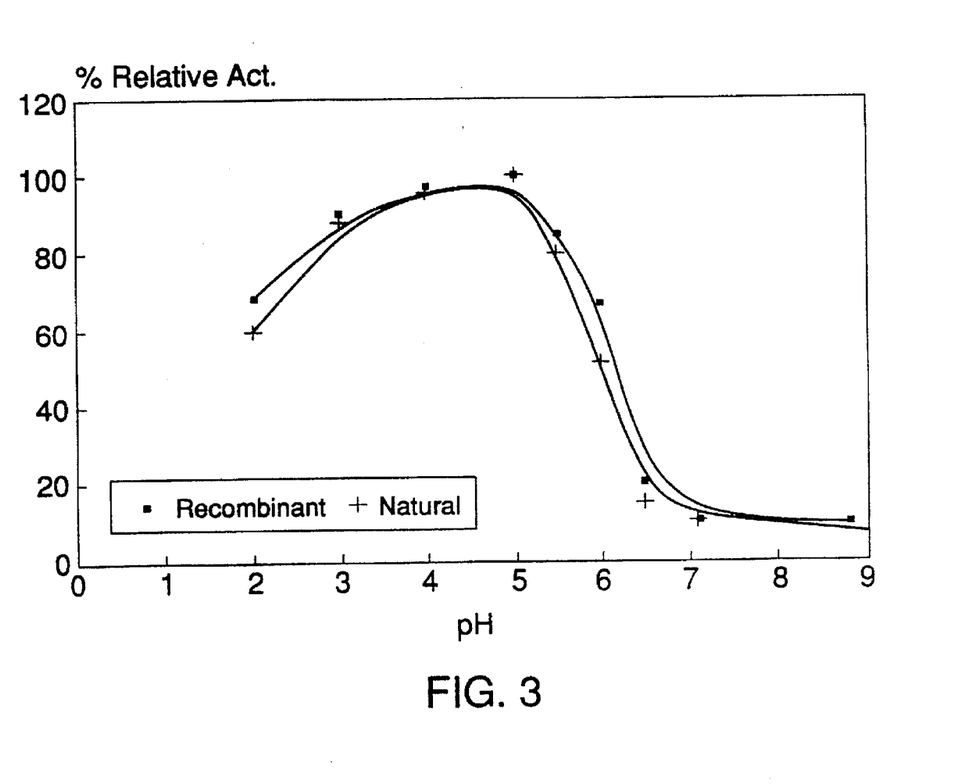
FIG. 3 Influence of the pH on the determination of enzymatic activity expressed as % relative activity with respect to the maximum value for natural and recombinant dextranase.

Relative activity values (expressed as % maximum activity) were measured at different pH values from 2 to 9. The optimum pH value for the activity was estimated as 5. It was similar for both natural and recombinant enzymes (FIG. 3)

Figure 4:
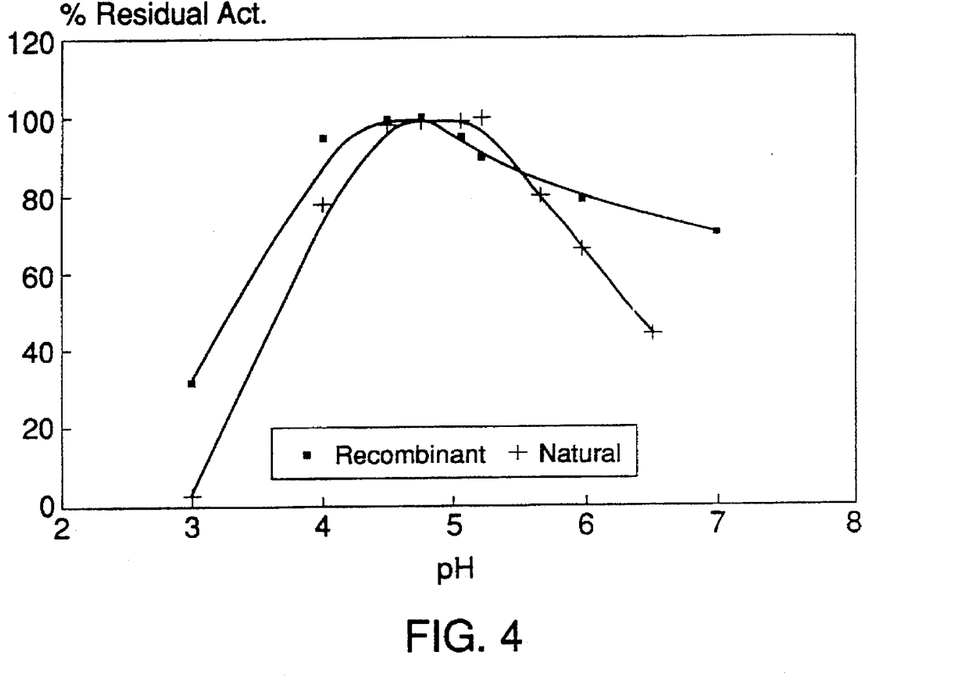
FIG. 4 pH stability of natural and recombinant dextranase expressed as % residual activity (100% activity at pH 4.5) after 30 min. incubation at 50° C. at a given pH.
Figure 5:
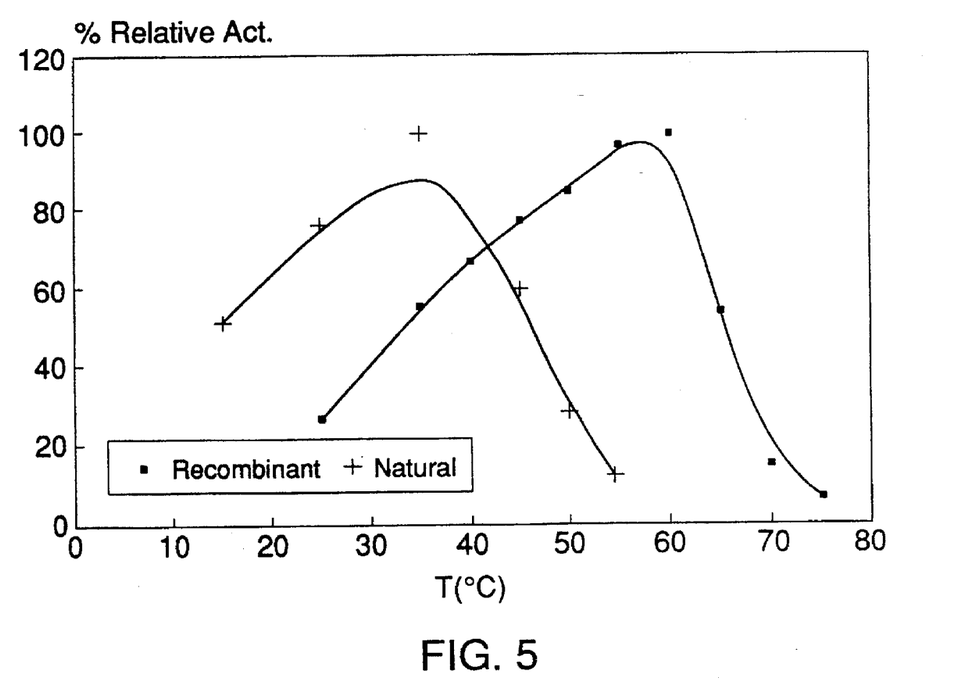
FIG. 5 Influence of the temperature on the determination of enzymatic activity expressed as % relative activity with respect to the maximum value for natural and recombinant dextranase.

An increase of stability (measured as % residual activity after incubating the enzyme at 50° C. during 30 min.) of the recombinant enzyme in relation to the natural enzyme in the pH range between 5.5 and 7 was observed (FIG. 4). Besides that, the stability of both enzymes was markedly affected at pH below 3.5.

c) Influence of Temperature on Enzymatic Activity; Stability at Different Temperatures Relative activities of both enzymes were measured at different temperatures (FIG. 5). Both natural and recombinant enzymes are sensitive to temperature changes; the first showed optimum activity at 30°–40° C. and the second at 55°–60° C. A temperature variation of +/—10° C. implied a 20–40% decrease in maximum activity for both natural and recombinant enzymes.

The thermal stability of the enzyme was determined varying the temperature and measuring the residual activity at different incubation times. The enzyme denaturing reaction corresponded to first order kinetics:

$$\log(\% \text{ Act.}) = k*t+2 \quad (1),$$

wherein

%Act.=% of enzyme residual activity.

k=denaturing reaction rate constant.

t=time.

Figure 6:
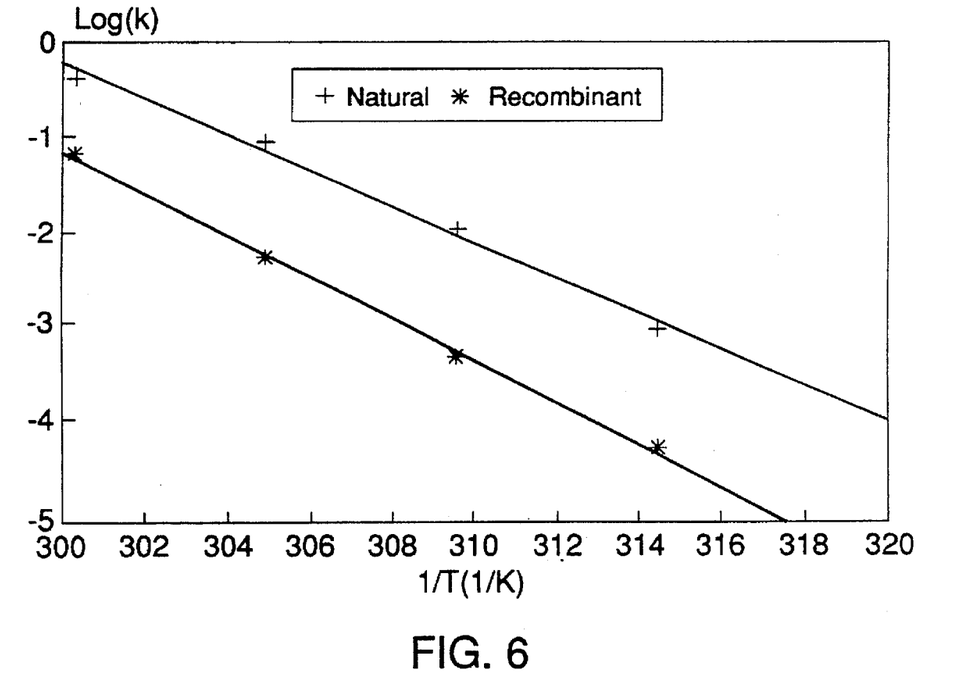
FIG. 6 Thermal stability of natural and recombinant dextranase expressed as denaturing reaction rate from Arrhenius equation. Plotting of logk (k=denaturing rate constant) versus 1/T (T=temperature in Kelvin×10$^5$).

After plotting log(k) against 1/T expressed in Kelvin (according to Arrhenius' equation, FIG. 6) and considering equation (1), the half-life time ($t_{1/2}$) was estimated at different temperatures, as the time when the enzyme loses 50% of its initial activity. The results attained at 30° and 50° C. are presented in Table 2.

TABLE 2

Comparison of the calculated half-life time ($t_{1/2}$) for natural and recombinant enzymes.

| Temperature | Half-life time ($t_{1/2}$) | |
|---|---|---|
| (°C.) | Natural dextranase | Recombinant dextranase |
| 30 | 5 months | 11 years |
| 50 | 42 minutes | 7.6 hours |

The fact that the recombinant enzyme has higher thermal stability and higher stability towards pH at the range between 5.5 and 7 than the natural enzyme and also an optimum temperature activity at 55°–60° C., represents an advantage for its use in the sugar industry.

TABLE 3

Sequenced fragment from a genomic cone containing the dextranase gene of the fungus *Penicillium minioluteum*. The cloned cDNA started at nucleotide #1080 and ended at nucleotide #3187. The four ATG's located in the 5' region of the cDNA sequence started at nucleotides #1124, #1133, #1190 and #1226, respectively. Amino acid sequence of the secreted dextranase enzyme deduced from the dextranase cDNA sequence of the fungus *Penicillium minioluteum*. The underlined sequences correspond to peptide sequences from recombinant dextranse prouduced by MPDEX1 strain.

| | | | | | | |
|---|---|---|---|---|---|---|
| GGCATAGTAA | TCCCGACAGC | CGAGTATGAT | GGAGCTTCTT | CGGATAATGA | | 50 |
| TAGCGCCACC | AGACCTTGCT | TGAGCTGGAG | AGCTAAAACA | TTAAACGCCA | | 100 |
| CACGACCAAC | ACTCTCATTA | GTTGCGATAG | ATGATGCTCG | GAGCTGTTGA | | 150 |
| AACTCAGAAA | TTCCTTCTAT | GCGGGGTCTC | CAAGATCGAT | CCTGGGGGAT | | 200 |
| GTGAATACTA | CGGTGGACCT | AATTGACGCC | TTGACAGGTG | ATGTTAAGCG | | 250 |
| AACCAAGGAA | GAATAATCTG | GGGCTAGATG | AAGATGTTGA | GCTGTAAGGT | | 300 |
| ACGGTACGTT | CCTATTGGCT | TTATCGGAGC | TTCTCCGGGT | TACTCAGTCT | | 350 |
| TTCCGGGAGC | ATGATCATTT | TTGTATTGTC | CAATAGTAAG | CAGAAACTGA | | 400 |
| GAGCCACCAC | AAACTCAAAA | CCTCGGTAGC | GAAGTTTCCC | GGAACCAGTC | | 450 |
| AGGATTCTCA | GAAACTGTGC | TCGTGTTGCG | GGGAATCCGC | ATTCTACGTC | | 500 |
| GTCTGGAGCA | AGGAAATGTT | CGTGCTGGAT | TGAGGAGGAT | AGGTAGGTTG | | 550 |
| GAGAATCTCT | TCAGCTAACC | AATCTATAAG | CATGCTCCGG | TAACCTTTAG | | 600 |
| AGTTTCACAT | TCAACGTAAT | TTCCAAGATA | GCCAGAGCGT | CCTTGAATTA | | 650 |
| CTATGTAGAA | ATCCTAAAAT | TTCCCCTGTA | AAATGCAAGT | CAACGAGATG | | 700 |
| CGTGCCCTCA | ATGTCTCTCG | GCGCTACCCC | GGAAATGATG | CATAAGGCCA | | 750 |
| AGAATGTCAC | CCGGTAACTT | TTTCTTCAGA | ATATCCTAAG | ATTTCCATCA | | 800 |
| AACACAGTCG | AATAGGTCAA | TGCTCGCGAG | AGACTTTCTG | CCTTCACTCT | | 850 |
| ACGTCCTACT | CATAGAAGTT | CAACGGCTCA | ATTCCGGGGT | AATCTAGAGT | | 900 |
| TTGGACCTCA | AGGGAGATGT | TGCAACAAAT | TGTACTAGAA | CGATGCGCTT | | 950 |
| GCTTTCCAAT | ACAGTAGTTG | ACTTCATATA | GCTTCCAACA | AAAGGGATGG | | 1000 |
| GGATGAAGGC | TCTATAGCGA | GAAGTCTATA | AGAAAGTGTC | CTCATACCTG | | 1050 |
| TATCTCTCAG | TCGTTCGAGA | ACAATCCCGG | AAACTATCTT | ATCTTGCGAG | | 1100 |
| AAAGAAGACA | ATATCTCAAA | CTTATGGCCA | CAATGCTAAA | GCTACTTGCG | | 1150 |
| TTGACCCTTG | CAATTAGCGA | GTCCGCCATT | GGAGCAGTCA | TGCACCCACC | | 1200 |
| TGGCAATTCT | CATCCCGGTA | CCCAT | | | | 1246 |

| | | | | | | |
|---|---|---|---|---|---|---|
| | | | ATG | GGC | ACT | ACG | AAT | AAT | ACC |
| | | | Met | Gly | Thr | Thr | Asn | Asn | Thr |
| | | | 1 | | | 5 | | | |

| CAT | TGC | GGC | GCC | GAT | TTC | TGT | ACC | TGG | TGG | CAT | GAT | TCA | GGG | 1288 |
|---|---|---|---|---|---|---|---|---|---|---|---|---|---|---|
| His | Cys | Gly | Ala | Asp | Phe | Cys | Thr | Try | Trp | His | Asp | Ser | Gly | |
| | 10 | | | | | 15 | | | | | 20 | | | |

| GAG | ATC | AAT | ACG | CAG | ACA | CCT | GTC | CAA | CCA | GGG | AAC | GTG | CGC | 1330 |
|---|---|---|---|---|---|---|---|---|---|---|---|---|---|---|
| Glu | Ile | Asn | Thr | Gln | Thr | Pro | Val | Gln | Pro | Gly | Asn | Val | Arg | |
| | | | 25 | | | | | 30 | | | | | 35 | |

| CAA | TCT | CAC | AAG | TAT | TCC | GTG | CAA | GTG | AGC | CTA | GCT | GGT | ACA | 1372 |
|---|---|---|---|---|---|---|---|---|---|---|---|---|---|---|
| Gln | Ser | His | Lys | Tyr | Ser | Val | Gln | Val | Ser | Leu | Ala | Gly | Thr | |
| | | | | 40 | | | | | 45 | | | | | |

| AAC | AAT | TTT | CAT | GAC | TCC | TTT | GTA | TAT | GAA | TCG | ATC | CCC | CGG | 1414 |
|---|---|---|---|---|---|---|---|---|---|---|---|---|---|---|

TABLE 3-continued

Sequenced fragment from a genomic cone containing the dextranase gene of the fungus *Penicillium minioluteum*. The cloned cDNA started at nucleotide #1080 and ended at nucleotide #3187. The four ATG's located in the 5' region of the cDNA sequence started at nucleotides #1124, #1133, #1190 and #1226, respectively. Amino acid sequence of the secreted dextranase enzyme deduced from the dextranase cDNA sequence of the fungus *Penicillium minioluteum*. The underlined sequences correspond to peptide sequences from recombinant dextranse prouduced by MPDEX1 strain.

| Asn | Asn | Phe | His | Asp | Ser | Phe | Val | Tyr | Glu | Ser | Ile | Pro | Arg | |
|---|---|---|---|---|---|---|---|---|---|---|---|---|---|---|
| 50 | | | | 55 | | | | | 60 | | | | | |
| AAC Asn | GGA Gly | AAT Asn | GGT Gly | CGC Arg | ATC Ile | TAT Tyr | GCT Ala | CCC Pro | ACC Thr | GAT Asp | CCA Pro | CCC Pro | AAC Asn | 1456 |
| | 65 | | | | 70 | | | | | 75 | | | | |
| AGC Ser | AAC Asn | ACA Thr | CTA Leu | GAT Asy | TCA Ser | AGT Ser | GTG Val | GAT Asp | GAT Asp | GGA Gly | ATC Ile | TCG Ser | ATT Ile | 1498 |
| | | 80 | | | | 85 | | | | | 90 | | | |
| GAG Glu | CCT Pro | AGT Ser | ATC Ile 95 | GGC Gly | CTT Leu | AAT Asn | ATG Met | GCA Ala 100 | TGG Trp | TCC Ser | CAA Gln | TTC Phe | GAG Glu 105 | 1540 |
| TAC Tyr | AGC Ser | CAC His | GAT Asp | GTA Val 110 | GAT Asp | GTA Val | AAG Lys | ATC Ile | CTG Leu 115 | GCC Ala | ACT Thr | GAT Asp | GGC Gly | 1582 |
| TCA Ser 120 | TCG Ser | TTG Leu | GGC Gly | TCG Ser | CCA Pro 125 | AGT Ser | GAT Asp | GTT Val | GTT Val | ATT Ile 130 | CGC Arg | CCC Pro | GTC Val | 1624 |
| TCA Ser | ATC Ile 135 | TCC Ser | TAT Tyr | GCG Ala | ATT Ile | TCT Ser 140 | CAG Gln | TCT Ser | GAC Asp | GAT Asp | GGT Gly 145 | GGG Gly | ATT Ile | 1666 |
| GTC Val | ATC Ile | CGG Arg 150 | GTC Val | CCA Pro | GCC Ala | GAT Asp | GCG Ala 155 | AAC Asn | GGC Gly | CGC Arg | AAA Lys | TTT Phe 160 | TCA Ser | 1708 |
| GTT Val | GAG Glu | TTC Phe | AAA Lys | ACT Thr | GAC Asp | CTG Leu | TAC Tyr | ACA Thr | TTC Phe | CTC Leu | TCT Ser | GAT Asp | GGC Gly | 1750 |
| | | 165 | | | | | 170 | | | | | 175 | | |
| AAC Asn | GAG Glu | TAC Tyr | GTC Val | ACA Thr 180 | TCG Ser | GGA Gly | GGC Gly | AGC Ser | GTC Val 185 | GTC Val | GGC Gly | GTT Val | GAG Glu | 1792 |
| CCT Pro 190 | ACC Thr | AAC Asn | GCA Ala | CTT Leu | GTG Val 195 | ATC Ile | TTC Phe | GCA Ala | AGT Ser | CCG Pro 200 | TTT Phe | CTT Leu | CCT Pro | 1834 |
| TCT Ser | GGC Gly 205 | ATG Met | ATT Ile | CCT Pro | CAT His | ATG Met 210 | ACA Thr | CCC Pro | GAC Asp | AAC Asn | ACG Thr 215 | CAG Gln | ACC Thr | 1876 |
| ATG Met | ACG Thr | CCA Pro 220 | GGT Gly | CCT Pro | ATC Ile | AAT Asn | AAC Asn 225 | GGC Gly | GAC Asp | TGG Trp | GGC Gly | GCC Ala 230 | AAG Lys | 1918 |
| TCA Ser | ATT Ile | CTT Leu | TAC Tyr 235 | TTC Phe | CCA Pro | CCA Pro | GGT Gly | GTA Val 240 | TAC Tyr | TGG Trp | ATG Met | AAC Asn | CAA Gln 245 | 1960 |
| GAT Asp | CAA Gln | TCG Ser | GGC Gly | AAC Asn | TCG Ser | GGG Gly | AAG Lys | TTA Leu | GGA Gly | TCT Ser | AAT Asn | CAT His | ATA Ile | 2002 |
| | | | | 250 | | | | | 255 | | | | | |
| CGT Arg | CTA Leu | AAC Asn | TCG Ser | AAC Asn | ACT Thr | TAC Tyr | TGG Trp | GTC Val | TAC Tyr | CTT Leu | GCC Ala | CCC Pro | GGT Gly | 2044 |
| 260 | | | | | 265 | | | | | 270 | | | | |
| GCG Ala | TAC Tyr 275 | GTG Val | AAG Lys | GGT Gly | GCT Ala | ATA Ile 280 | GAG Glu | TAT Tyr | TTT Phe | ACC Thr | AAG Lys 285 | CAG Gln | AAC Asn | 2086 |

TABLE 3-continued

Sequenced fragment from a genomic cone containing the dextranase gene of the fungus *Penicillium minioluteum*. The cloned cDNA started at nucleotide #1080 and ended at nucleotide #3187. The four ATG's located in the 5' region of the cDNA sequence started at nucleotides #1124, #1133, #1190 and #1226, respectively. Amino acid sequence of the secreted dextranase enzyme deduced from the dextranase cDNA sequence of the fungus *Penicillium minioluteum*. The underlined sequences correspond to peptide sequences from recombinant dextrase prouduced by MPDEX1 strain.

| | | | | | | | | | | | | | | |
|---|---|---|---|---|---|---|---|---|---|---|---|---|---|---|
| TTC Phe | TAT Tyr | GCA Ala 290 | ACT Thr | GGT Gly | CAT His | GGT Gly | ATC Ile 295 | CTA Leu | TCG Ser | GGT Gly | GAA Glu | AAC Asn 300 | TAT Tyr | 2128 |
| GTT Val | TAC Tyr | CAA Gln | GCC Ala 305 | AAT Asn | GCC Ala | GGC Gly | GAC Asp | AAC Asn 310 | TAC Tyr | ATT Ile | GCA Ala | GTC Val | AAG Lys 315 | 2170 |
| AGC Ser | GAT Asp | TCA Ser | ACC Thr | AGC Ser 320 | CTC Leu | CGG Arg | ATG Met | TGG Trp | TGG Trp 325 | CAC His | AAT Asn | AAC Asn | CTT Leu | 2212 |
| GGG Gly 330 | GGT Gly | GGT Gly | CAA Gln | ACA Thr | TGG Trp 335 | TAC Tyr | TGC Cys | GTT Val | GGC Gly | CCG Pro 340 | ACG Thr | ATC Ile | AAT Asn | 2254 |
| GCG Ala | CCA Pro 345 | CCA Pro | TTC Phe | AAT Asn | ACT Thr | ATG Met 350 | GAT Asp | TTC Phe | AAT Asn | GGA Gly | AAT Asn 355 | TCT Ser | GGC Gly | 2296 |
| ATC Ile | TCA Ser | AGT Ser 360 | CAA Gln | ATT Ile | AGC Ser | GAC Asp | TAT Tyr 365 | AAG Lys | CAG Gln | GTG Val | GGA Gly | GCC Ala 370 | TTC Phe | 2338 |
| TTC Phe | TTC Phe | CAG Gln | ACG Thr 375 | GAT Asp | GGA Gly | CCA Pro | GAA Glu | ATA Ile 380 | TAT Tyr | CCC Pro | AAT Asn | AGT Ser | GTC Val 385 | 2380 |
| GTG Val | CAC His | GAC Asc | GTC Val | TTC Phe | TGG Tro 390 | CAC His | GTC Val | AAT Asn | GAT Asc | GAT Asp 395 | GCA Ala | ATC Ile | AAA Lys | 2422 |
| ATC Ile 400 | TAC Tyr | TAT Tyr | TCG Ser | GGA Gly | GCA Ala 405 | TCT Ser | GTA Val | TCG Ser | CGG Arg | GCA Ala 410 | ACG Thr | ATC Ile | TGG Trp | 2464 |
| AAA Lys | TGT Cys 415 | CAC His | AAT Asn | GAC Asp | CCA Pro | ATC Ile 420 | ATC Ile | CAG Gln | ATG Met | GGA Gly | TGG Trp 425 | ACG Thr | TCT Ser | 2506 |
| CGG Arg | GAT Asp | ATC Ile 430 | AGT Ser | GGA Gly | GTG Val | ACA Thr | ATC Ile 435 | GAC Asp | ACA Thr | TTA Leu | AAT Asn | GTT Val 440 | ATT Ile | 2548 |
| CAC His | ACC Thr | CGC Arg | TAC Tyr 445 | ATC Ile | AAA Lys | TCG Ser | GAG Glu | ACG Thr 450 | GTG Val | GTG Val | CCT Pro | TCG Ser | GCT Ala 455 | 2590 |
| ATC Ile | ATT Ile | GGG Gly | GCC Ala | TCT Ser 460 | CCA Pro | TTC Phe | TAT Tyr | GCA Ala | AGT Ser 465 | GGG Gly | ATG Met | AGT Ser | CCT Pro | 2632 |
| GAT Asp | TCA Ser | AGA Arg | AAG Lys | TCC Ser | ATA Ile 475 | TCC Ser | ATG Met | ACG Thr | GTT Val | TCA Ser 480 | AAC Asn | GTT Val | GTT Val | 2674 |
| 470 | | | | | | | | | | | | | | |
| TGC Cys | GAG Glu 485 | GGT Gly | CTT Leu | TGC Cys | CCG Pro | TCC Ser 490 | CTA Leu | TTC Phe | CGC Arg | ATC Ile | ACA Thr 495 | CCC Pro | CTT Leu | 2716 |
| CAG Gln | AAC Asn | TAC Tyr 500 | AAA Lys | AAT Asn | TTT Phe | GTT Val | GTC Val 505 | AAA Lys | AAT Asn | GTG Val | GCT Ala 510 | TTC Phe | CCA Pro | 2758 |
| GAC Asp | GGG Gly | CTA Leu | CAG Gln | ACG Thr | AAT Asn | AGT Ser | ATT Ile | GGC Gly | ACA Thr | GGA Gly | GAA Glu | AGC Ser | ATT Ile | 2800 |

TABLE 3-continued

Sequenced fragment from a genomic cone containing the dextranase gene of the fungus Penicillium minioluteum. The cloned cDNA started at nucleotide #1080 and ended at nucleotide #3187. The four ATG's located in the 5' region of the cDNA sequence started at nucleotides #1124, #1133, #1190 and #1226, respectively. Amino acid sequence of the secreted dextranase enzyme deduced from the dextranase cDNA sequence of the fungus Penicillium minioluteum. The underlined sequences correspond to peptide sequences from recombinant dextranse prouduced by MPDEX1 strain.

|  |  |  | 515 |  |  |  |  |  |  | 520 |  |  |  | 525 |  |
|---|---|---|---|---|---|---|---|---|---|---|---|---|---|---|---|
| ATT | CCA | GCC | GCA | TCT | GGT | CTA | ACG | ATG | GGA | CTG | AAT | ATC | TCC |  | 2842 |
| Ile | Pro | Ala | Ala | Ser | Gly | Leu | Thr | Met | Gly | Leu | Asn | Ile | Ser |  |  |
|  |  |  |  | 530 |  |  |  |  | 535 |  |  |  |  |  |  |
| AAC | TGG | ACT | GTT | GGT | GGA | CAA | AAA | GTG | ACT | ATG | GAG | AAC | TTT |  | 2884 |
| Asn | Trp | Thr | Val | Gly | Gly | Gln | Lys | Val | Thr | Met | Glu | Asn | Phe |  |  |
| 540 |  |  |  |  | 545 |  |  |  |  | 550 |  |  |  |  |  |
| CAA | GCC | AAT | AGC | CTG | GGG | CAG | TTC | AAT | ATT | GAC | GGC | AGC | TAT |  | 2926 |
| Gln | Ala | Asn | Ser | Leu | Gly | Gln | Phe | Asn | Ile | Asp | Gly | Ser | Tyr |  |  |
|  | 555 |  |  |  |  | 560 |  |  |  |  | 565 |  |  |  |  |
| TGG | GGG | GAG | TGG | CAG | ATT | AGC | TGA | ATTCCAGCTC |  | TCGGAGCGCG |  |  |  |  | 2970 |
| Trp | Gly | Glu | Trp | Gln | Ile | Ser | *** |  |  |  |  |  |  |  |  |
|  |  | 570 |  |  |  | 574 |  |  |  |  |  |  |  |  |  |

| TGAGTGCTTC | TACCCGCTCC | TTTACCCTTG | TCGAGAGATA | AAGGCATAAG | 3020 |
|---|---|---|---|---|---|
| TTAGCTCATG | TGAAGGCGAT | TTCAGTTCAT | TCTCTCTTTT | TGGAGCTTAT | 3070 |
| TTCCTGTTCG | ACCAATTGTG | ACACCAACTT | GCCTTTCAAA | AGACGTGGAC | 3120 |
| GATATGTGTA | CGGTAATCAG | TCAAATGAAC | GTCAACATTC | ATTTAATAAG | 3170 |
| GACATTTCCA | GGTTTCCTTA | CTCTGTCGAT | TATGCCTAAC | TCGGGTTGAT | 3220 |
| GTCTTGTCAG | GATGGAAAAT | CTCGTTGTGT | ACTTCCAGTG | AAATGGGCAG | 3270 |
| GGCTAAGCCC | TAAACCCTAA | CGCATACAAT | TTGTAGGCAC | CTACCCATGT | 3320 |
| AAGTTCACAC | CCAGTCGACT | TATAAGTCTA | GATATTTATG | CTATGCAGGC | 3370 |
| TCTGGAATGA | TTTACATTCC | ATGCTATACA | TAGTTATTTG | CAAGAATTTG | 3420 |
| CAGACGAGAT | AAAAATCAAT | GGACGAATAA | TCACGCATTA | CTCCACAGGC | 3470 |
| TCATGCCACG | GAGCAAGGGT | TCCCCCGAAT | CTAGGCCAGA | CCGGGATGAT | 3520 |
| ATTCAACCGA | TTCTTTTTGC | AGTAACTATC | TCCGTACGAG | CTGCACGAGC | 3570 |
| TAAACGGATT | ATATAAAGGT | GCTAACTGAG | CATTGGATCC | GTCAGTTATA | 3620 |
| TGAAATGCA |  | 3629 |  |  |  |

What is claimed is:

1. An isolated and purified DNA comprised in a dextranase gene sequence, said DNA comprising nucleotides No. 1226 to No. 2947 of Seq. Id. No. 1, wherein said DNA codes for an enzyme having dextranase activity.

2. The isolated and purified DNA according to claim 1, wherein said DNA codes for a dextranase enzyme of the fungus *Penicillium minioluteum*.

3. The isolated and purified DNA according to claim 2, wherein said DNA further includes a promotor region of the dextranase gene from the fungus *Penicillium minioluteum*.

4. The isolated and purified DNA according to claim 3, wherein said promoter region is nucleotides No. 1 to No. 1079 of Seq. Id. No. 1.

5. The isolated and purified DNA according to claim 2, wherein said DNA further includes nucleotides No. 1080 to No. 1225 of Seq. Id. No. 1, which code for signal peptides.

6. An isolated and purified DNA from a micro-organism specie other than said *Penicillium minioluteum* of claim 2, comprising DNA that hybridizes with nucleotides No. 1226 to No. 2947 of Seq. Id. No. 1, wherein said DNA codes for an enzyme having dextranase activity.

7. An isolated and pitied DNA coding for an enzyme with dextranase activity, said enzyme comprising the amino acid sequence of Seq. Id. No. 2.

8. An expression vector comprising said DNA of claim 1 or said DNA of claim 7.

9. The expression vector according to claim 8, wherein said expression vector is able to direct the expression of a protein with dextranase activity in a suitable host cell.

10. The expression vector according to claim 9, wherein said expression vector is able to direct the expression of a protein with dextranase activity in a yeast.

11. The expression vector according to claim 10, wherein said expression vector is able to direct the expression of a protein with dextranase activity in the yeast *Pichia pastoris*.

12. The expression vector according to claim 11, wherein said expression vector is plasmid pPDEX1.

13. A host cell transformed with said expression vector of claim 8.

14. The host cell according to claim 13, wherein said host cell is a yeast.

15. The host cell according to claim 14, wherein said yeast is *Pichia pastoris*.

16. The host cell according to claim 15, wherein said *Pichia pastoris* is strain MPDEX1.

17. A proteinaceous substance having dextranase activity comprising a polypeptide comprising the amino acid sequence of Seq. Id. No. 2, wherein said proteinaceous substance has a specific activity in the range of 900 to 1000 U/mg of protein.

18. The proteinaceous substance according to claim 17, wherein said proteinaceous substance has an optimum temperature for enzymatic activity in the range between 55° C. and 60° C., a N-glycosylation percentage of about 13–15% and a half-life time of about 7.6 hours at 50° C.

19. A method for producing a proteinaceous substance having dextranase activity, which comprises expressing in a yeast said DNA according to claim 1 coding for said dextranase enzyme, and isolating said dextranase enzyme produced from the growth medium.

20. The method according to claim 19, wherein said yeast is *Pichia pastoris*.

21. A method for hydrolyzing dextran which comprises contacting dextran under suitable dextran depolymerization conditions with a dextranase enzyme from cells producing said dextranase enzyme wherein said dextranase enzyme is said proteinaceous substance of claim 17, said proteinaceous substance of claim 18, said proteinaceous substance produced according to the method of claim 19, or said proteinaceous substance produced according to the method of claim 20.

22. The method of claim 21, which further comprises recovering dextran depolymerization products produced.

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 3629 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( B ) STRAIN: Penicillium minioluteum HI-4

( x i ) SEQUENCE DESCRIPTION: SEQ ID NO: 1:

```
GGCATAGTAA  TCCCGACAGC  CGAGTATGAT  GGAGCTTCTT  CGGATAATGA  TAGCGCCACC        60

AGACCTTGCT  TGAGCTGGAG  AGCTAAAACA  TTAAACGCCA  CACGACCAAC  ACTCTCATTA       120

GTTGCGATAG  ATGATGCTCG  GAGCTGTTGA  AACTCAGAAA  TTCCTTCTAT  GCGGGGTCTC       180

CAAGATCGAT  CCTGGGGGAT  GTGAATACTA  CGGTGGACCT  AATTGACGCC  TTGACAGGTG       240

ATGTTAAGCG  AACCAAGGAA  GAATAATCTG  GGGCTAGATG  AAGATGTTGA  GCTGTAAGGT       300
```

```
ACGGTACGTT CCTATTGGCT TTATCGGAGC TTCTCCGGGT TACTCAGTCT TTCCGGGAGC    360
ATGATCATTT TTGTATTGTC CAATAGTAAG CAGAAACTGA GAGCCACCAC AAACTCAAAA    420
CCTCGGTAGC GAAGTTTCCC GGAACCAGTC AGGATTCTCA GAAACTGTGC TCGTGTTGCG    480
GGGAATCCGC ATTCTACGTC GTCTGGAGCA AGGAAATGTT CGTGCTGGAT TGAGGAGGAT    540
AGGTAGGTTG GAGAATCTCT TCAGCTAACC AATCTATAAG CATGCTCCGG TAACCTTTAG    600
AGTTTCACAT TCAACGTAAT TTCCAAGATA GCCAGAGCGT CCTTGAATTA CTATGTAGAA    660
ATCCTAAAAT TTCCCTGTA AAATGCAAGT CAACGAGATG CGTGCCCTCA ATGTCTCTCG     720
GCGCTACCCC GGAAATGATG CATAAGGCCA AGAATGTCAC CCGGTAACTT TTCTTCAGA    780
ATATCCTAAG ATTTCCATCA AACACAGTCG AATAGGTCAA TGCTCGCGAG AGACTTTCTG    840
CCTTCACTCT ACGTCCTACT CATAGAAGTT CAACGGCTCA ATTCGGGGT AATCTAGAGT     900
TTGGACCTCA AGGGAGATGT TGCAACAAAT TGTACTAGAA CGATGCGCTT GCTTCCAAT    960
ACAGTAGTTG ACTTCATATA GCTTCCAACA AAAGGGATGG GGATGAAGGC TCTATAGCGA   1020
GAAGTCTATA AGAAAGTGTC CTCATACCTG TATCTCTCAG TCGTTCGAGA ACAATCCCGG   1080
AAACTATCTT ATCTTGCGAG AAAGAAGACA ATATCTCAAA CTTATGGCCA CAATGCTAAA   1140
GCTACTTGCG TTGACCCTTG CAATTAGCGA GTCCGCCATT GGAGCAGTCA TGCACCCACC   1200
TGGCAATTCT CATCCCGGTA CCCATATGGG CACTACGAAT AATACCCATT GCGGCGCCGA   1260
TTTCTGTACC TGGTGGCATG ATTCAGGGGA GATCAATACG CAGACACCTG TCCAACCAGG   1320
GAACGTGCGC CAATCTCACA AGTATTCCGT GCAAGTGAGC CTAGCTGGTA CAAACAATTT   1380
TCATGACTCC TTTGTATATG AATCGATCCC CCGGAACGGA AATGGTCGCA TCTATGCTCC   1440
CACCGATCCA CCCAACAGCA ACACACTAGA TTCAAGTGTG GATGATGGAA TCTCGATTGA   1500
GCCTAGTATC GGCCTTAATA TGGCATGGTC CCAATTCGAG TACAGCCACG ATGTAGATGT   1560
AAAGATCCTG GCCACTGATG GCTCATCGTT GGGCTCGCCA AGTGATGTTG TTATTCGCCC   1620
CGTCTCAATC TCCTATGCGA TTTCTCAGTC TGACGATGGT GGGATTGTCA TCCGGGTCCC   1680
AGCCGATGCG AACGGCCGCA AATTTTCAGT TGAGTTCAAA ACTGACCTGT ACACATTCCT   1740
CTCTGATGGC AACGAGTACG TCACATCGGG AGGCAGCGTC GTCGGCGTTG AGCCTACCAA   1800
CGCACTTGTG ATCTTCGCAA GTCCGTTTCT TCCTTCTGGC ATGATTCCTC ATATGACACC   1860
CGACAACACG CAGACCATGA CGCCAGGTCC TATCAATAAC GGCGACTGGG GCGCCAAGTC   1920
AATTCTTTAC TTCCCACCAG GTGTATACTG GATGAACCAA GATCAATCGG GCAACTCGGG   1980
GAAGTTAGGA TCTAATCATA TACGTCTAAA CTCGAACACT TACTGGGTCT ACCTTGCCCC   2040
CGGTGCGTAC GTGAAGGGTG CTATAGAGTA TTTTACCAAG CAGAACTTCT ATGCAACTGG   2100
TCATGGTATC CTATCGGGTG AAAACTATGT TTACCAAGCC AATGCCGGCG ACAACTACAT   2160
TGCAGTCAAG AGCGATTCAA CCAGCCTCCG GATGTGGTGG CACAATAACC TTGGGGGTGG   2220
TCAAACATGG TACTGCGTTG GCCCGACGAT CAATGCGCCA CCATTCAATA CTATGGATTT   2280
CAATGGAAAT TCTGGCATCT CAAGTCAAAT TAGCGACTAT AAGCAGGTGG GAGCCTTCTT   2340
CTTCCAGACG GATGGACCAG AAATATATCC CAATAGTGTC GTGCACGACG TCTTCTGGCA   2400
CGTCAATGAT GATGCAATCA AAATCTACTA TTCGGGAGCA TCTGTATCGC GGGCAACGAT   2460
CTGGAAATGT CACAATGACC CAATCATCCA GATGGGATGG ACGTCTCGGG ATATCAGTGG   2520
AGTGACAATC GACACATTAA ATGTTATTCA CACCCGCTAC ATCAAATCGG AGACGGTGGT   2580
GCCTTCGGCT ATCATTGGGG CCTCTCCATT CTATGCAAGT GGGATGAGTC CTGATTCAAG   2640
AAAGTCCATA TCCATGACGG TTTCAAACGT TGTTTGCGAG GGTCTTTGCC CGTCCCTATT   2700
```

| | | | | | |
|---|---|---|---|---|---|
| CCGCATCACA | CCCCTTCAGA | ACTACAAAAA | TTTTGTTGTC | AAAAATGTGG | CTTTCCCAGA | 2760 |
| CGGGCTACAG | ACGAATAGTA | TTGGCACAGG | AGAAAGCATT | ATTCCAGCCG | CATCTGGTCT | 2820 |
| AACGATGGGA | CTGAATATCT | CCAACTGGAC | TGTTGGTGGA | CAAAAAGTGA | CTATGGAGAA | 2880 |
| CTTTCAAGCC | AATAGCCTGG | GGCAGTTCAA | TATTGACGGC | AGCTATTGGG | GGGAGTGGCA | 2940 |
| GATTAGCTGA | ATTCCAGCTC | TCGGAGCGCG | TGAGTGCTTC | TACCCGCTCC | TTTACCCTTG | 3000 |
| TCGAGAGATA | AAGGCATAAG | TTAGCTCATG | TGAAGGCGAT | TTCAGTTCAT | TCTCTCTTTT | 3060 |
| TGGAGCTTAT | TTCCTGTTCG | ACCAATTGTG | ACACCAACTT | GCCTTTCAAA | AGACGTGGAC | 3120 |
| GATATGTGTA | CGGTAATCAG | TCAAATGAAC | GTCAACATTC | ATTAATAAG | GACATTTCCA | 3180 |
| GGTTTCCTTA | CTCTGTCGAT | TATGCCTAAC | TCGGGTTGAT | GTCTTGTCAG | GATGGAAAAT | 3240 |
| CTCGTTGTGT | ACTTCCAGTG | AAATGGGCAG | GGCTAAGCCC | TAAACCCTAA | CGCATACAAT | 3300 |
| TTGTAGGCAC | CTACCCATGT | AAGTTCACAC | CCAGTCGACT | TATAAGTCTA | GATATTTATG | 3360 |
| CTATGCAGGC | TCTGGAATGA | TTTACATTCC | ATGCTATACA | TAGTTATTTG | CAAGAATTTG | 3420 |
| CAGACGAGAT | AAAAATCAAT | GGACGAATAA | TCACGCATTA | CTCCACAGGC | TCATGCCACG | 3480 |
| GAGCAAGGGT | TCCCCCGAAT | CTAGGCCAGA | CCGGGATGAT | ATTCAACCGA | TTCTTTTTGC | 3540 |
| AGTAACTATC | TCCGTACGAG | CTGCACGAGC | TAAACGGATT | ATATAAAGGT | GCTAACTGAG | 3600 |
| CATTGGATCC | GTCAGTTATA | TGAAATGCA | | | | 3629 |

( 2 ) INFORMATION FOR SEQ ID NO: 2:

( i ) SEQUENCE CHARACTERISTICS:
        ( A ) LENGTH: 574 amino acids
        ( B ) TYPE: amino acid
        ( C ) STRANDEDNESS: unknown
        ( D ) TOPOLOGY: unknown     ( i i ) MOLECULE TYPE: protein     ( i i i ) HYPOTHETICAL: NO     ( v i ) ORIGINAL SOURCE:
        ( B ) STRAIN: Penicillium minioluteum HI-4

( x i ) SEQUENCE DESCRIPTION: SEQ ID NO: 2:

```
Met Gly Thr Thr Asn Asn Thr His Cys Gly Ala Asp Phe Cys Thr Trp
 1               5                  10                  15

Trp His Asp Ser Gly Glu Ile Asn Thr Gln Thr Pro Val Gln Pro Gly
                20                  25                  30

Asn Val Arg Gln Ser His Lys Tyr Ser Val Gln Val Ser Leu Ala Gly
            35                  40                  45

Thr Asn Asn Phe His Asp Ser Phe Val Tyr Glu Ser Ile Pro Arg Asn
        50                  55                  60

Gly Asn Gly Arg Ile Tyr Ala Pro Thr Asp Pro Asn Ser Asn Thr
 65                  70                  75                  80

Leu Asp Ser Ser Val Asp Asp Gly Ile Ser Ile Glu Pro Ser Ile Gly
                85                  90                  95

Leu Asn Met Ala Trp Ser Gln Phe Glu Tyr Ser His Asp Val Asp Val
                100                 105                 110

Lys Ile Leu Ala Thr Asp Gly Ser Ser Leu Gly Ser Pro Ser Asp Val
            115                 120                 125

Val Ile Arg Pro Val Ser Ile Ser Tyr Ala Ile Ser Gln Ser Asp Asp
        130                 135                 140

Gly Gly Ile Val Ile Arg Val Pro Ala Asp Ala Asn Gly Arg Lys Phe
145                 150                 155                 160
```

-continued

| | | | | | | | | | | | | | | |
|---|---|---|---|---|---|---|---|---|---|---|---|---|---|---|
| Ser | Val | Glu | Phe | Lys 165 | Thr | Asp | Leu | Tyr 170 | Thr | Phe | Leu | Ser | Asp | Gly | Asn 175 |
| Glu | Tyr | Val | Thr 180 | Ser | Gly | Gly | Ser | Val 185 | Val | Gly | Val | Glu | Pro 190 | Thr | Asn |
| Ala | Leu | Val 195 | Ile | Phe | Ala | Ser | Pro 200 | Phe | Leu | Pro | Ser | Gly 205 | Met | Ile | Pro |
| His | Met 210 | Thr | Pro | Asp | Asn | Thr 215 | Gln | Thr | Met | Thr | Pro 220 | Gly | Pro | Ile | Asn |
| Asn 225 | Gly | Asp | Trp | Gly | Ala 230 | Lys | Ser | Ile | Leu | Tyr 235 | Phe | Pro | Pro | Gly | Val 240 |
| Tyr | Trp | Met | Asn | Gln 245 | Asp | Gln | Ser | Gly | Asn 250 | Ser | Gly | Lys | Leu | Gly 255 | Ser |
| Asn | His | Ile | Arg 260 | Leu | Asn | Ser | Asn | Thr 265 | Tyr | Trp | Val | Tyr | Leu 270 | Ala | Pro |
| Gly | Ala | Tyr 275 | Val | Lys | Gly | Ala | Ile 280 | Glu | Tyr | Phe | Thr | Lys 285 | Gln | Asn | Phe |
| Tyr | Ala 290 | Thr | Gly | His | Gly | Ile 295 | Leu | Ser | Gly | Glu | Asn 300 | Tyr | Val | Tyr | Gln |
| Ala 305 | Asn | Ala | Gly | Asp | Asn 310 | Tyr | Ile | Ala | Val | Lys 315 | Ser | Asp | Ser | Thr | Ser 320 |
| Leu | Arg | Met | Trp | Trp 325 | His | Asn | Asn | Leu | Gly 330 | Gly | Gly | Gln | Thr | Trp 335 | Tyr |
| Cys | Val | Gly | Pro 340 | Thr | Ile | Asn | Ala | Pro 345 | Pro | Phe | Asn | Thr | Met 350 | Asp | Phe |
| Asn | Gly | Asn | Ser 355 | Gly | Ile | Ser | Ser | Gln 360 | Ile | Ser | Asp | Tyr | Lys 365 | Gln | Val |
| Gly | Ala 370 | Phe | Phe | Phe | Gln | Thr 375 | Asp | Gly | Pro | Glu | Ile 380 | Tyr | Pro | Asn | Ser |
| Val 385 | Val | His | Asp | Val | Phe 390 | Trp | His | Val | Asn | Asp 395 | Asp | Ala | Ile | Lys | Ile 400 |
| Tyr | Tyr | Ser | Gly | Ala 405 | Ser | Val | Ser | Arg | Ala 410 | Thr | Ile | Trp | Lys | Cys 415 | His |
| Asn | Asp | Pro | Ile 420 | Ile | Gln | Met | Gly | Trp 425 | Thr | Ser | Arg | Asp | Ile 430 | Ser | Gly |
| Val | Thr | Ile 435 | Asp | Thr | Leu | Asn | Val 440 | Ile | His | Thr | Arg | Tyr 445 | Ile | Lys | Ser |
| Glu | Thr 450 | Val | Val | Pro | Ser | Ala 455 | Ile | Ile | Gly | Ala | Ser 460 | Pro | Phe | Tyr | Ala |
| Ser 465 | Gly | Met | Ser | Pro | Asp 470 | Ser | Arg | Lys | Ser | Ile 475 | Ser | Met | Thr | Val | Ser 480 |
| Asn | Val | Val | Cys | Glu 485 | Gly | Leu | Cys | Pro | Ser 490 | Leu | Phe | Arg | Ile | Thr 495 | Pro |
| Leu | Gln | Asn | Tyr 500 | Lys | Asn | Phe | Val | Val 505 | Lys | Asn | Val | Ala | Phe 510 | Pro | Asp |
| Gly | Leu | Gln 515 | Thr | Asn | Ser | Ile | Gly 520 | Thr | Gly | Glu | Ser | Ile 525 | Ile | Pro | Ala |
| Ala | Ser 530 | Gly | Leu | Thr | Met | Gly 535 | Leu | Asn | Ile | Ser | Asn 540 | Trp | Thr | Val | Gly |
| Gly 545 | Gln | Lys | Val | Thr | Met 550 | Glu | Asn | Phe | Gln | Ala 555 | Asn | Ser | Leu | Gly | Gln 560 |
| Phe | Asn | Ile | Asp | Gly 565 | Ser | Tyr | Trp | Gly | Glu 570 | Trp | Gln | Ile | Ser | | |

( 2 ) INFORMATION FOR SEQ ID NO: 3:

(i) SEQUENCE CHARACTERISTICS:
    (A) LENGTH: 16 amino acids
    (B) TYPE: amino acid
    (C) STRANDEDNESS:
    (D) TOPOLOGY: linear (ii) MOLECULE TYPE: peptide (iii) HYPOTHETICAL: NO (xi) SEQUENCE DESCRIPTION: SEQ ID NO: 3:

```
Met Gly Thr Thr Asn Asn Thr His Cys Gly Ala Asp Phe Cys Thr Trp
 1               5                  10                  15
```

(2) INFORMATION FOR SEQ ID NO: 4:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: other nucleic acid (iii) HYPOTHETICAL: NO (xi) SEQUENCE DESCRIPTION: SEQ ID NO: 4:

ATGGGCACTA CGAATAATAC CCAT                                              24

(2) INFORMATION FOR SEQ ID NO: 5:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: other nucleic acid (iii) HYPOTHETICAL: NO (xi) SEQUENCE DESCRIPTION: SEQ ID NO: 5:

GGAAACCTGG AAATGTCCTT AT                                                22